(12) United States Patent
Skakoon

(10) Patent No.: US 9,113,850 B2
(45) Date of Patent: Aug. 25, 2015

(54) SALIVA COLLECTION DEVICE

(75) Inventor: James G. Skakoon, Saint Paul, MN (US)

(73) Assignee: Reflex Medical Corp., White Bear Lake, MN (US)

( * ) Notice: Subject to any disclaimer, the term of this patent is extended or adjusted under 35 U.S.C. 154(b) by 857 days.

(21) Appl. No.: 13/214,722

(22) Filed: Aug. 22, 2011

(65) Prior Publication Data

US 2012/0046574 A1    Feb. 23, 2012

Related U.S. Application Data

(60) Provisional application No. 61/375,685, filed on Aug. 20, 2010, provisional application No. 61/489,221, filed on May 23, 2011.

(51) Int. Cl.
  *A61B 5/00* (2006.01)
  *A61B 10/00* (2006.01)

(52) U.S. Cl.
  CPC ......... *A61B 10/0051* (2013.01); *A61B 10/0096* (2013.01)

(58) Field of Classification Search
  CPC ...... A61B 10/0051; A61B 5/083; A61B 5/42; A61B 5/411; A61B 5/097; A61B 10/0096; B01L 2300/046
  USPC ................................ 422/562; 4/258; 600/573
  See application file for complete search history.

(56) References Cited

U.S. PATENT DOCUMENTS

| | | | |
|---|---|---|---|
| 630,225 A * | 8/1899 | Hodgerny | .......................... 4/259 |
| 3,518,164 A | 6/1970 | Andelin et al. | |
| 4,091,802 A | 5/1978 | Columbus | |
| 4,283,498 A | 8/1981 | Schlesinger | |
| 4,411,163 A | 10/1983 | White | |
| 4,580,577 A | 4/1986 | O'Brien et al. | |
| 4,589,548 A | 5/1986 | Fay | |
| 4,628,547 A * | 12/1986 | Baker | ................................ 4/259 |
| 4,741,346 A | 5/1988 | Wong et al. | |
| 4,761,379 A | 8/1988 | Williams et al. | |
| 4,768,238 A | 9/1988 | Kleinberg et al. | |
| 4,813,931 A | 3/1989 | Hauze | |
| 4,817,632 A | 4/1989 | Schramm | |
| 4,932,081 A * | 6/1990 | Burns | ............................... 4/258 |
| 5,050,616 A | 9/1991 | Wolff et al. | |
| 5,238,655 A | 8/1993 | Laible et al. | |

(Continued)

FOREIGN PATENT DOCUMENTS

WO    WO 2007/068094 A1    6/2007

*Primary Examiner* — Devin Henson
*Assistant Examiner* — David J McCrosky
(74) *Attorney, Agent, or Firm* — Christensen Fonder P.A.

(57) ABSTRACT

A device for collecting oral fluid includes a mouthpiece with a fluid inlet connected to a collection chamber. The collection chamber includes a collecting vessel, a venting outlet, and an access port. The venting outlet may be covered by a liquid-impervious or resistant membrane, such as a hydrophobic membrane, and the access port is suitable for removing some or all of the collected fluid. This arrangement allows a saliva donor to continuously spit saliva and blow air into the closed collection chamber, without pressure build-up in the collection chamber, and without the need for the donor to release from the device until the desired oral fluid volume is collected. A valve, including a check valve may be in the saliva flow stream and baffles and structure creating a tortuous path may be utilized to keep saliva away from the membrane.

23 Claims, 6 Drawing Sheets

(56) References Cited

U.S. PATENT DOCUMENTS

| | | | |
|---|---|---|---|
| 5,260,031 A | 11/1993 | Seymour | |
| 5,339,829 A | 8/1994 | Thieme et al. | |
| 5,393,496 A | 2/1995 | Seymour | |
| 5,562,639 A | 10/1996 | Lynn et al. | |
| 5,795,773 A * | 8/1998 | Read et al. | 435/287.5 |
| 5,981,293 A | 11/1999 | Charlton | |
| 6,150,178 A | 11/2000 | Cesarczyk et al. | |
| 6,152,887 A | 11/2000 | Blume | |
| 6,416,715 B1 | 7/2002 | Gambert et al. | |
| 6,582,415 B1 | 6/2003 | Fowles et al. | |
| 6,718,563 B1 | 4/2004 | Kreiensieck | |
| 7,114,403 B2 | 10/2006 | Wu et al. | |
| 7,374,723 B2 | 5/2008 | Wuske et al. | |
| 7,387,899 B1 | 6/2008 | D'Angelo | |
| 7,544,324 B2 | 6/2009 | Tung et al. | |
| 7,850,922 B2 | 12/2010 | Gallagher et al. | |
| 8,318,107 B2 * | 11/2012 | Rieder et al. | 422/404 |
| 2004/0077093 A1 * | 4/2004 | Pan | 436/37 |
| 2004/0133128 A1 | 7/2004 | Guan et al. | |
| 2005/0096563 A1 * | 5/2005 | Liang | 600/573 |
| 2006/0057027 A1 | 3/2006 | Hudak et al. | |
| 2008/0017577 A1 | 1/2008 | Yi et al. | |
| 2008/0020477 A1 * | 1/2008 | Pronovost | 436/95 |
| 2009/0024058 A1 * | 1/2009 | Blowick et al. | 600/582 |
| 2009/0093064 A1 | 4/2009 | Kolesnychenko | |
| 2009/0117665 A1 | 5/2009 | Tung et al. | |
| 2009/0216213 A1 | 8/2009 | Muir et al. | |
| 2009/0305315 A1 | 12/2009 | Gandola et al. | |
| 2009/0306610 A1 | 12/2009 | Heuvel et al. | |
| 2012/0021375 A1 * | 1/2012 | Binner et al. | 433/89 |
| 2012/0282681 A1 * | 11/2012 | Teixeira et al. | 435/287.2 |

* cited by examiner

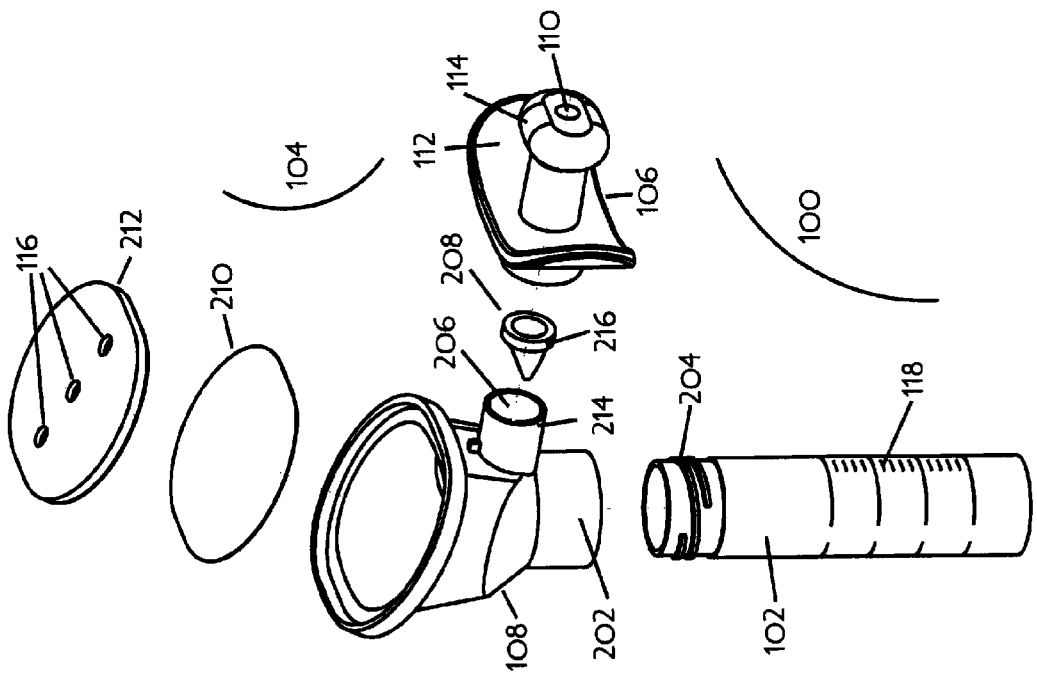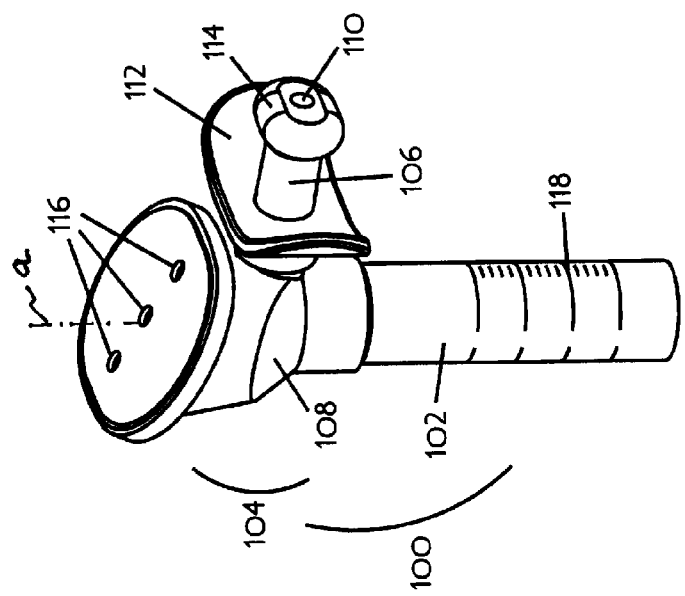

SALIVA COLLECTION DEVICE

RELATED APPLICATIONS

The present application claims the benefit of U.S. Provisional Application No. 61/375,685 filed Aug. 20, 2010, and U.S. Provisional Application No. 61/489,221, filed May 23, 2011, which applications are hereby incorporated by reference herein in their entirety.

FIELD OF THE INVENTION

The present invention relates to devices for collecting saliva. In particular, the present invention relates to a saliva collection device wherein the donor can discharge saliva directly and continuously into a closed collection container. The present invention also relates to systems for collecting and chemically analyzing saliva.

BACKGROUND OF THE INVENTION

Bodily fluids are collected for various reasons, including diagnosing illness, simple therapeutic removal, determining pregnancy, confirming or establishing levels of therapeutic agents, determining drug abuse, and profiling DNA composition. Blood, urine, and saliva are among the commonly collected bodily fluids for some or all of these purposes.

Collecting blood and urine is routine in health care environments for any of the aforementioned reasons. However, collecting these fluids has some negative characteristics for some purposes such as, for example, determining drug abuse, especially in environments outside of traditional health care settings.

Screening for drugs of abuse is performed by health professionals, law enforcement personnel, and government or private employers, among others. Sample collection occurs in numerous different venues, including roadside stops, corporate offices, clinical labs, medical clinics, and in donors' homes. These venues are commonly classified as in-home, point-of-care, or laboratory. Substances of abuse that are commonly screened for include alcohol, cannabis, barbiturates, opioids, cocaine, amphetamines, and hallucinogens.

Obtaining a blood sample requires vascular access with a venipuncture needle, which is highly invasive and potentially dangerous to both donor and administrator. Urine, although less invasive to obtain than blood, brings up issues of privacy that limit its usefulness for drug testing in many environments. Moreover, urine samples are more easily adulterated if continuous donor observation is prevented by privacy requirements. For many such tests and testing environments, blood or urine collection is difficult, if not impossible, making saliva collection an appealing alternative. Saliva is less invasive to obtain than either blood or urine, and does not invoke privacy concerns to the same extent as does urine.

DNA testing is used for purposes of paternity, genealogy, disease susceptibility, and forensics, among others. Blood samples, buccal swabs, and saliva are commonly used for DNA tests. Collecting saliva is less invasive than collecting blood, and saliva collection can provide a larger, and therefore perhaps more reliable sample than buccal swabs.

Saliva samples are commonly collected by one of two methods: intra-oral sponge absorption and direct expectoration. An example of the first is U.S. Pat. No. 4,580,577 to O'Brien, et al, which discloses an absorbent mass that is masticated by the donor until saturated. The mass is placed in a squeezing device to expel saliva into a holding chamber, out of which a test aliquot can be removed. Sponge or sponge-like absorption methods are disclosed in numerous other patents, teaching variations such as added reagents, salivation promoters, preservatives, flavorings, chemical stabilizers, and a plurality of samples, among others.

U.S. Pat. No. 4,817,632 to Schramm
U.S. Pat. No. 5,339,829 to Thieme, et al.
U.S. Pat. No. 5,260,031 to Seymour
U.S. Pat. No. 5,393,496 to Seymour
U.S. Pat. No. 5,981,293 to Charlton
U.S. Pat. No. 6,150,178 to Cesarczyk, et al.
U.S. Pat. No. 6,416,715 to Gambert, et al.
U.S. Pat. No. 7,114,403 to Wu, et al.
U.S. Pat. No. 7,374,723 to Wuske, et al.
U.S. Pat. No. 7,387,899 to D'Angelo
U.S. Pat. No. 7,544,324 to Tung, et al.
U.S. Pat. No. 7,850,922 to Gallagher, et al.
U.S. Patent App. No. 20090117665 to Tung, et al.
U.S. Patent App. No. 20060057027 to Hudak, et al.
are some examples of prior art saliva absorption patents.

An example of a commercially available saliva collector using intra-oral absorption is the Salivette® made by Sarstedt AG & Co. The donor removes a cylindrical cotton or synthetic swab from the tube-like container, inserts the swab into the mouth, chews it until it becomes saliva-saturated, then returns it to the tube. A cap is applied that seals the saliva inside the tube.

An example of a sample collection device based on direct expectoration is disclosed in U.S. Pat. No. 3,518,164 to Andelin, et al. This device includes a tube-like collector, an attached funnel, a stabilizing base, and a threaded sealing cap. The donor spits into the funnel, saliva collects in the tube to the desired volume, the funnel is removed, and the donated sample is sealed with the cap.

Other prior art example patents teaching variations of direct saliva expectoration collection include:
U.S. Pat. No. 4,741,346 to Wong, et al.
U.S. Pat. No. 4,283,498 to Schlesinger
U.S. Pat. No. 4,589,548 to Fay
U.S. Pat. No. 4,761,379 to Williams, et al.
U.S. Pat. No. 4,768,238 to Kleinberg, et al.
U.S. Pat. No. 4,932,081 to Bums
U.S. Patent App. No. 200500965693 to Liang U.S. Patent App. No. 20090216213 to Muir et al.

Additional References Cited

U.S. Pat. No. 4,091,802 to Columbus
U.S. Pat. No. 4,411,163 to White
U.S. Pat. No. 5,050,616 to Wolff, et al.
U.S. Pat. No. 5,238,655 to Laible, et al.
U.S. Pat. No. 5,562,639 to Lynn, et al.
U.S. Pat. No. 6,152,887 to Blume
U.S. Pat. No. 6,718,563 to Kreiensieck
U.S. Patent App. No. 20040133128 to Guan, et al.
U.S. Patent App. No. 20080017577 to Vi, et al.
U.S. Patent App. No. 20090093064 to Kolesnychenko
U.S. Patent App. No. 20090305315 to Gandola, et al.
U.S. Patent App. No. 20090306610 to Van Den Heuvel, et al.
UltraSal-2™ Saliva Collection Device by Oasis Diagnostics Corporation More generally, there is a wide range of devices for collecting bodily fluids, with configurations dependent on the bodily fluid collected and the intended subsequent use of the fluid. For example, U.S. Pat. No. 4,813,931 to Hauze discloses a suction device for aspirating matter for disposal from the mouth and throat of pediatric patients. One embodiment of this invention is a typical vacuum collection vessel with an inlet, an outlet, and an air gap. In the U.S. Pat. No. 4,813,931 invention, the physician applies vacuum by mouth to the outlet tube and thereby to the collecting chamber, and a tube connected to the chamber transfers vacuum for aspiration to the aspiration site. An in-line, hydrophobic, liquid-impervious filter prevents the aspirated matter from reaching the physician. Another example, in this case for collecting blood, is disclosed in U.S. Pat. No. 5,238,655 to Laible, et al. This invention shows a similar arrangement of components, i.e. an inlet for capillary blood, a collection chamber, and an outlet, the outlet connected to a vacuum source. A hydrophobic membrane filter isolates the collected fluid from the outlet, thus allowing air to be withdrawn from the collection chamber by the vacuum source, yet preventing blood from being removed through the outlet.

Returning now specifically to the prior art for saliva collection, the prior art methods have several drawbacks. Intra-oral saliva absorption requires sponge or spongelike materials. These can adsorb saliva constituents, which may cause errors in subsequent analysis. The absorbent materials can cause discomfort for the donor, perhaps even precipitating a biological reaction. Expectoration into an open container avoids the drawbacks of oral absorption methods, but is a clumsy, unsanitary process. Donors may miss the funnel or container when spitting, may dribble sputum onto themselves or the administrator, and may spill the container, all with negative consequences. The requirement for repetitious and sequential positioning and spitting is cumbersome and exhausting. Although the oral absorption devices generally avoid the clumsiness of the prior art direct collection devices, they have their own aforementioned drawbacks. Expectorating into a closed container though an inlet tube, or straw-like mouthpiece, would be an improvement for collecting saliva, but doing so continuously would be impossible because of pressure build-up within the collection chamber. Creating a vent hole would vent the pressure, but would also allow inadvertent or intentional escape of the collected fluid. Having the donor repeatedly release from and recouple to the mouthpiece would again be clumsy and would result in dribbling of sputum from the mouthpiece during release.

There remains a need for an improved saliva collection device.

SUMMARY OF THE INVENTION

The present invention is a device for collecting oral fluid that includes a mouthpiece with a fluid inlet connected to a collection chamber. The collection chamber includes a collecting vessel, a venting outlet, and an access port. The venting outlet may be covered by a liquid-impervious membrane, and the access port is suitable for removing some or all of the collected fluid. This arrangement allows a saliva donor to continuously spit saliva and blow air into the closed collection chamber, without pressure build-up in the collection chamber, and without the need for the donor to release from the device until the desired oral fluid volume is collected.

Embodiments of the present invention can also include additional advantageous features. For example, a one-way check valve or a tester- or user-operated valve in line with the fluid inlet can prevent fluid from coming back out of the collection chamber into the fluid inlet, even if the device is tipped. Thus, the valve captures the fluid inside the device, preventing accidental leaking, until fluid removal is desired.

Embodiments of the present invention can also include various physically, chemically, and biologically active agents. For example, anti-foaming or de-foaming compounds can be added to the device to reduce the foaming propensity of the collected fluid. Also, preservatives can be used to preserve the collected fluid, and test reagents can be added for preconditioning or direct chemical analysis.

The present invention can be a component of any system requiring a saliva sample. For example, a plurality of lateral flow immunoassay strips can be included in a test system for which the present invention can be a part. For example, the disclosed saliva collection device can be physically separated from the test system for saliva collection, then coupled or recoupled to the test system for assay. Alternatively, the present invention can include a transfer container that allows some or all of the collected saliva to be transferred from the collection device to a lateral flow assay system.

Alternatively, the present invention can be incorporated as an integral sub-system of an assay test system. Saliva can be accumulated and held separate from the assaying portion, if necessary, until an adequate volume is collected, then be allowed to enter the assaying portion.

It is therefore a feature and advantage of embodiments of the invention to provide an improved saliva collection device for use whenever oral fluid must be collected. It is also a feature and advantage of embodiments of the invention to collect oral fluid without using absorbent sponges or swabs, either in or outside the mouth. It is also an object of this invention to provide a saliva collection device wherein the saliva is collected in a closed container. It is also a feature and advantage of embodiments of the invention to provide a saliva collection device for collecting saliva in a closed container for which the donor may remain joined to the device throughout the donation. It is also a feature and advantage of embodiments of the invention to provide a device for which the donor may decouple from and recouple to the device without substantial loss of any accumulated saliva. It is also a feature and advantage of embodiments of the invention to provide a saliva collection device wherein the saliva is collected in a closed container that can be accessed for saliva removal.

DESCRIPTION OF THE DRAWINGS

FIG. 1 is a perspective view of a preferred embodiment of the present invention.

FIG. 2 is an exploded perspective view of the embodiment shown in FIG. 1.

DETAILED DESCRIPTION

Figure 4:
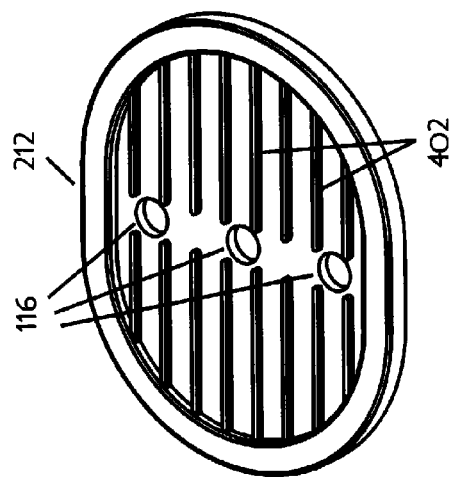
FIG. 4 is a detail perspective view of the inside surface of cover 212.

Referring to FIG. 1, there is shown a saliva collection device 100, which is an example embodiment of the present invention. This embodiment comprises a collection vessel 102 and a header assembly 104. Header assembly 104 includes a mouthpiece 106 and a header housing 108, that includes a receptacle portion 202. The mouthpiece 106 includes a saliva inlet 110, a mouthguard 112, and bulbous region 114 and a saliva passageway 115. Header assembly 104 also includes vent holes 116. The collection vessel 102, which is transparent in this embodiment, has gradations 118 showing the volume of fluid contained therein.

The device has an axis a which is coextensive with axis of the vessel 102. The header housing includes an upper chamber wall 122 with a upwardly oriented vent face portion 126, a converging portion 128.

Now referring to FIG. 2, which is an exploded view of FIG. 1 showing the components comprising the FIG. 1 embodiment of saliva collection device 101. Header assembly 104 includes a receptacle portion 202 into which collection vessel 102 is removably attached. In this case, receptacle portion 202 includes internal threads (not shown) to removably mate with threads 204 of collection vessel 102. Header housing 108 includes an inlet 206. A valve 208, such as a one-way check valve, here shown as a duckbill-style valve, is assembled into inlet 206. Header assembly 104 also includes venting membrane 210 and cover 212. Cover 212 includes the aforementioned vent holes 116.

The area of the filter membrane 202, that is, its "footprint", is larger than the largest cross sectional area of the header chamber taken at a plane p normal to the device axis a and is twice as large as the area a2 of the cross section of the vessel.

Figure 3:
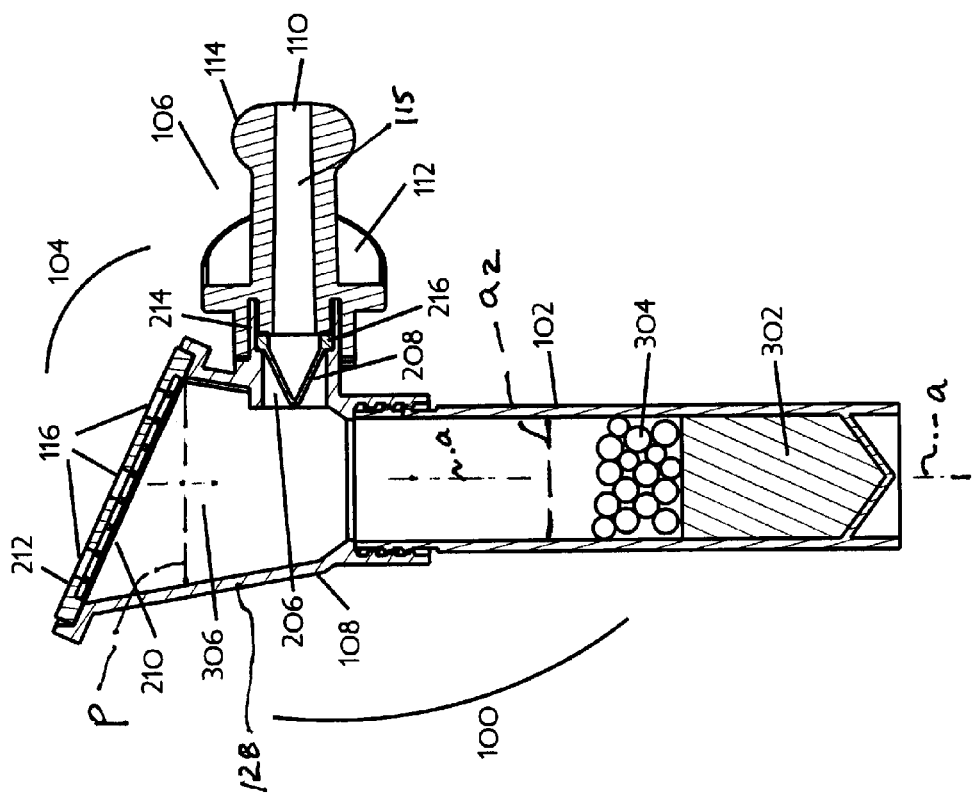
FIG. 3 is a cross-section view of the embodiment shown in FIG. 1 drawn through the common symmetric center lines of the assembly.

FIG. 3 is a cross section view, which shows additional details of construction of collection device 101. Collection vessel 102 is shown with a collected volume of saliva 302. Salival foam 304 may also be expectorated by an oral fluid donor along with the air and oral fluid. This salival foam 304 will sit atop saliva 302 in either collection vessel 102 or in the header chamber 306 (described below). Collection vessel 102 is removably attached to housing 108 of header assembly 104. Header assembly 104 includes a head space 306, which is enclosed on its upper end by venting membrane 210 and cover 212. Cover 212 and venting membrane 210 are attached to housing 108. Any of various bonding methods known in the art can be used to sandwich-bond venting membrane between housing 108 and cover 212. One suitable method, used in this embodiment, is ultrasonic welding. Referring briefly to FIG. 4, cover 212 includes a plurality of vent holes 116 as well as a maze-like pattern of ribs 402 on its inner side.

Returning to FIG. 3, valve 208 is shown in its assembled position within inlet 206 of housing 108 in header assembly 104. Valve 208 is held in place by a cylindrical portion 214 (also see FIG. 2) of mouthpiece 106. Mouthpiece 106 is bonded to inlet 206 using any suitable bonding method. One such suitable method, used in this embodiment, is solvent bonding using, for example, methyl ethyl ketone. Once valve 208 is captured by mouthpiece 106, a cylindrical ring 216 (also see FIG. 2) of valve 208 forms a leak-free seal with housing 108, which is the common method of seal used with valves of this style. Mouthpiece 106 includes saliva inlet 110, which is in fluid communication through valve 208 with head space 306, collection vessel 102, and also venting membrane 210 and, in turn, vent holes 116 of cover 212. Mouthpiece 106 includes enlargement configured as a bulbous portion 114, which comprises a smooth bulb-like structure.

Mouthguard 112 is a convenient stop or marker for proper insertion into the mouth of the donor. Mouthguard 112 also separates the saliva-contaminated region from the non-contaminated portions of oral fluid collection device 101, thereby allowing a test administrator to avoid touch contact with saliva. Enlargement 114 provides a tactile structure for a donor's lips and tongue, and aids in proper positioning and retention in the mouth. In one preferred embodiment, mouthpiece 106, along with mouthguard 112 and enlargement 114 are formed from a soft, pliable material to reduce the likelihood of dental damage during residence in the mouth. One suitable material, used in this embodiment, is flexible polyvinyl chloride (PVC).

Saliva, driven by the donor's spitting action and blowing action, enters saliva inlet 110 of mouthpiece 106. Saliva and air flow through valve 208 by this action, then enter head space 306 through inlet 206. Valve 208 prevents reverse flow of any expectorant, and assures that oral fluid and air is captured by the saliva collection device 101 once expelled by the donor. Valve 208 can be any configuration of one-way flow valve known in the art that meets the needed performance requirements for flow and crack pressure. Examples of suitable configurations include duck-bill style valves, rubber disk valves, and spring-loaded ball valves. Alternatively, valve 208 can be an active valve selectively opened and closed on demand by the donor or administrator by, for example, a push button actuator.

As the expelled oral fluid enters head space 306 the liquid component flows by gravity into collection vessel 102. Any expelled salival foam 304 resides atop the liquid saliva 302.

Air expelled by the donor (and air displaced by the collected oral fluid) is vented though the vent holes 116, thus avoiding pressure build-up inside the saliva collection device 100, which would prevent further flow of oral fluid. Venting membrane 210 can be a hydrophobic filter membrane, which will readily allow air to pass with little impediment, yet block liquids from passing under pressures encountered in normal use. A suitable example membrane is a hydrophobic pTFE filter media with a 1.0 micron pore size. Another suitable example membrane, used in this preferred embodiment, is known by the trade name Versapore® R, and is available from Pall Corporation. A suitable pore size of this membrane is, for example, 3.0 microns. Cover 212, as previously explained, includes vent holes 116 and maze-like ribs 402 (FIG. 4). Cover 212 supports venting membrane 210, preventing damage from outward bowing due to internal pressure or from contact from outside by fingers or other objects. Ribs 402 of cover 212 provide a flow path to vent holes 116 from all locations of venting membrane 210.

The volume of head space 306, the surface area of venting membrane 210, the location and orientation of venting membrane 210, and the characteristics of venting membrane 210 are all important considerations for robust function of saliva collection device 100. It is imperative for proper function that venting membrane 210 remains unblocked so that it is able to vent expired air and relieve internal pressure. If venting membrane 210 is liquid-covered over its entire surface area, air will not pass through it. Typical hydrophobic membranes are not easily wetted by water and by many other aqueous solutions. Non-wetting liquids will bead up and roll off the surface of a hydrophobic material. Saliva, however, can exhibit much more aggressive wetting than does water, and can more easily compromise venting performance of a hydrophobic membrane. Moreover, salival foam also accumulates when oral fluid is collected. This salival foam, generally, contains an inadequate volume of saliva for subsequent use. A foam-covered hydrophobic membrane will not properly vent, just as if it were liquid-covered.

Referring still to FIG. 3, it is clear that head space 306 provides volume to accommodate foam even as collection vessel 102 becomes filled with saliva and salival foam. Furthermore, the non-horizontal slope of venting membrane 210 allows saliva to flow away from the surface of venting membrane 210 when saliva collection device 100 is in the normal saliva donation orientation, which is approximately represented in FIG. 3. Even if saliva collection device 100 is inadvertently or purposely reoriented, dropped, or shaken, any of which could cause saliva to contact the surface of venting membrane 210, saliva will flow away from venting membrane 210 in this shown donation orientation due to gravity and the membrane's hydrophobic nature. In addition, venting membrane 210 has a relatively large surface area, first to allow unimpeded flow of air during saliva donation, and second to reduce the likelihood that saliva or salival foam will block the entire surface of venting membrane 210. In this embodiment then, the components' orientation, volumetric capacities, and membrane surface areas are sized so that a suitable volume of saliva 302 can be obtained with minimal risk of venting membrane 210 becoming blocked by saliva 302 or salival foam 304 when collecting the target volume. Also, air generating by the donor's spitting and blowing action can pass relatively unimpeded, thus minimizing the effort required by the donor to an acceptable level.

Figure 5:
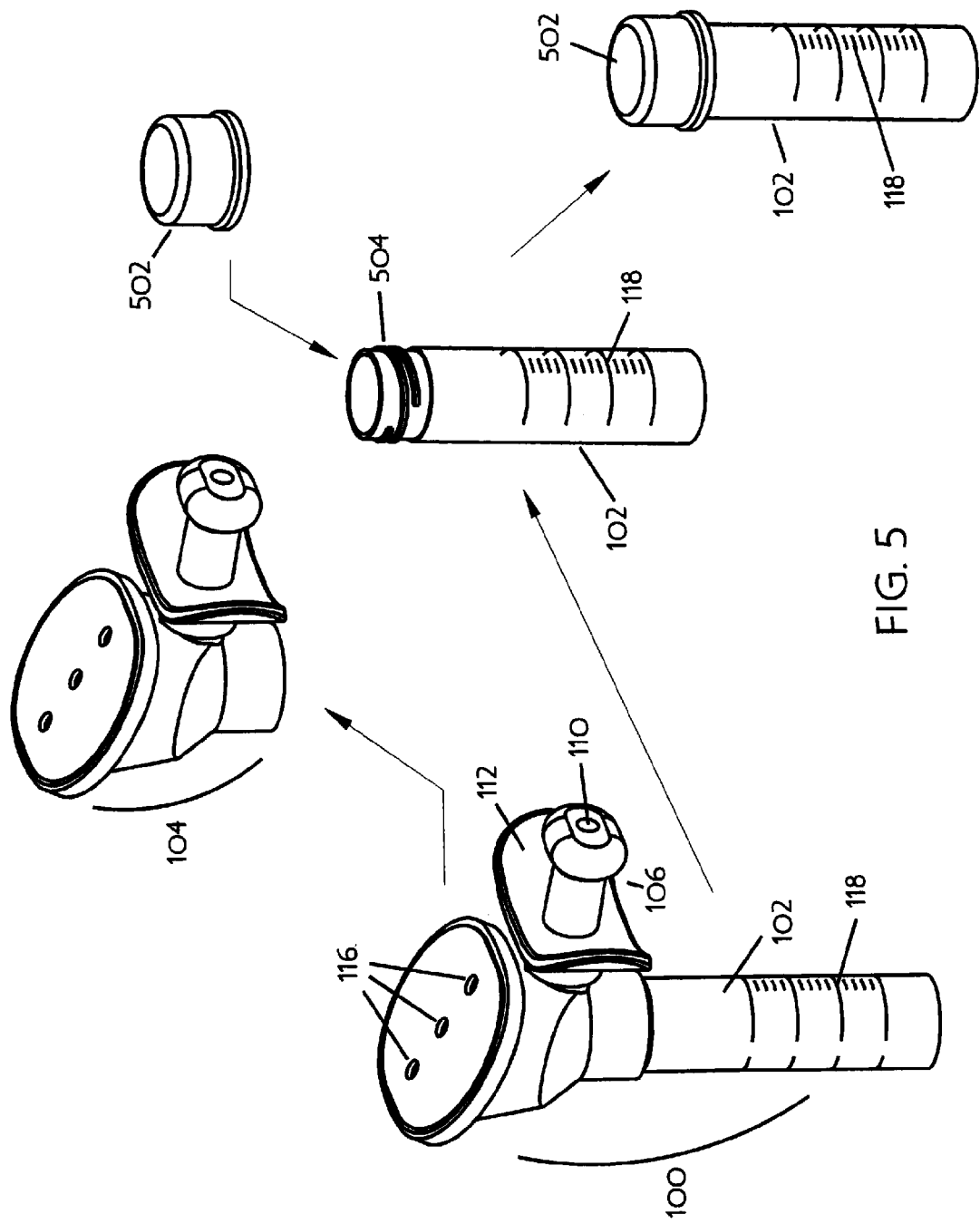
FIG. 5 is a multiple perspective view showing one typical use of the embodiment shown in FIG. 1.

In use, referring now to FIG. 5, a donor inserts mouthpiece 106 into the mouth, leaving mouthguard 112 outside the mouth. Enlargement 114 provides tactile feedback to aid in proper positioning and retention of saliva collection device 100. The donor spits and blows into mouthpiece 106 so that oral fluid, driven by spitting action and blowing action, enters saliva inlet 110. Expectorated saliva accumulates in collection vessel 102, and the accompanying air and potential pressure buildup is relieved through vent holes 116. Saliva entering saliva inlet 110 is captured inside saliva collection device 100 due to the valve disposed within inlet 206 and due to the venting membrane, which will not allow saliva to pass through it. Valve 208 prevents saliva from flowing or dribbling back out of saliva inlet 110, and venting membrane 210 (see FIG. 2) prevents saliva from exiting out vent holes 116, even if saliva collection device 100 is dropped, reoriented, or shaken.

The volume of accumulated saliva can be observed, typically by a test administrator or by the donor, and can be judged adequate by gradations 118. Once adequate saliva has been donated, collection vessel 102 is removed from header assembly 104. The saliva in collection vessel 102 can then be used for whatever purpose is desired, one example of which is to forward it to a testing laboratory for analysis. In that case, seal cap 502 can be applied to collection vessel 102, as shown in FIG. 5, allowing the saliva to be safely stored or transported as required for subsequent use.

In any case, opening 504, which is included in collection vessel 102 provides access to the accumulated saliva, either immediately upon removal from header assembly 104, or later upon removal of seal cap 502.

The present embodiment (FIGS. 1-5) also provides an easy method to collect multiple or additional aliquots of saliva, if desired or needed. This could be necessary, for example, if an instant read, point-of-collection test for drugs of abuse showed a positive result, and a confirmation test, with additional saliva, is required to be performed. In that case, another (or the same) collection vessel 102 can be attached to header assembly 104, and the donation procedure can be repeated.

Figure 6:
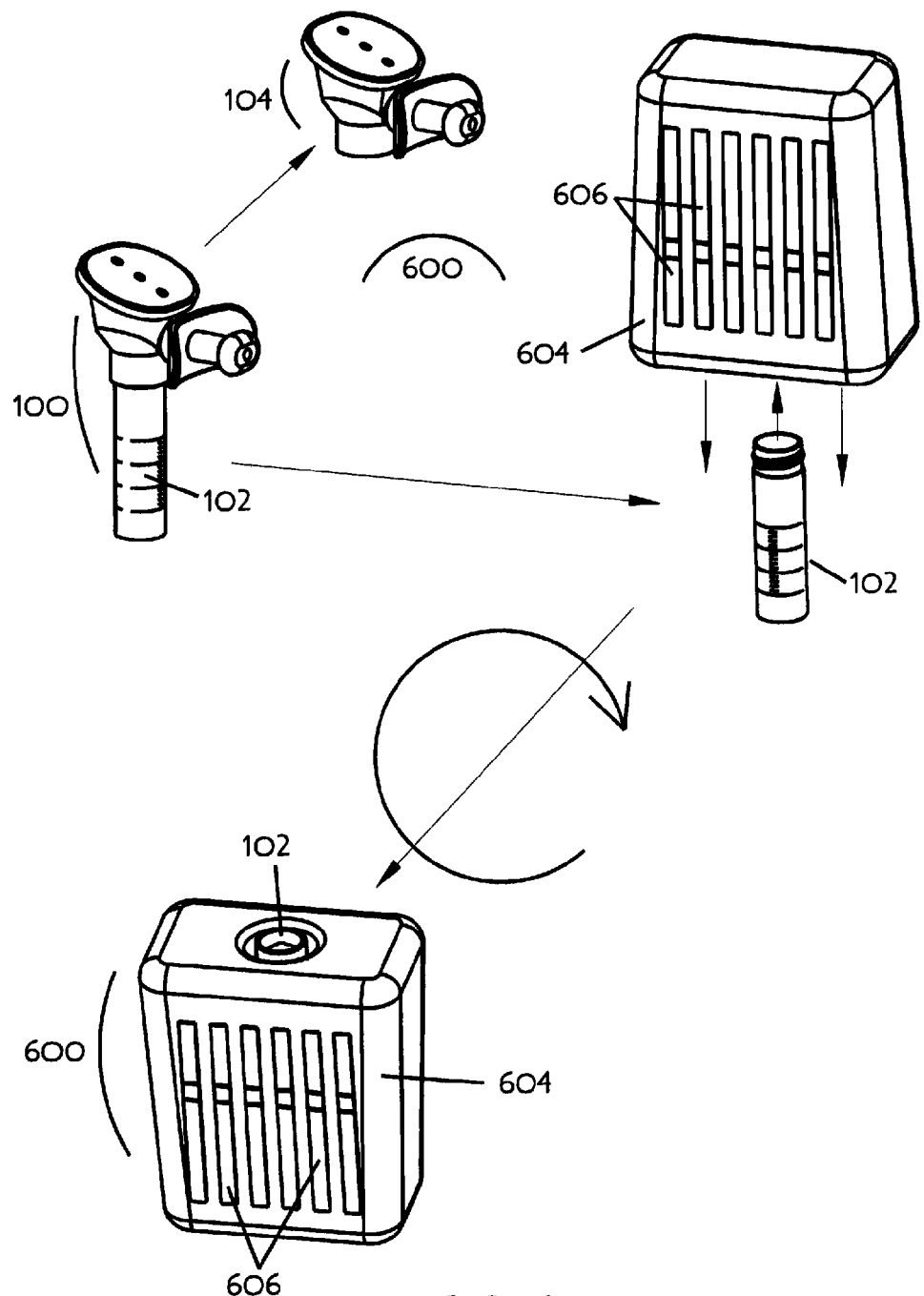
FIG. 6 is a multiple perspective view of an example system using the present invention.

Referring now to FIG. 6, an example embodiment is shown wherein the present invention is incorporated into an instant read test system, for example, for drugs of abuse.

Instant read system 600 includes a test housing 604 and a plurality of lateral flow immunoassay test strips 606 internal to test housing 604, and visible to an observer. Collection vessel 102 of saliva collection device 100 is separated from header assembly 104 after collection of the required volume of saliva. Collection vessel 102 is then sealably attached to test housing 604 by inserting one into the other. Test housing 604 includes suitable mating geometry such as connections, seals, and channels (not shown) to accept collection vessel 102 and manage the flow of saliva. Instant read system 600, with the attached collection vessel 102, is then inverted. Inversion allows the saliva held by collection vessel 102 to flow by gravity to make contact with test strips 606. Test methodology and reading of results is performed in accordance with normal practice for lateral flow immunoassay strip use.

Figure 7:
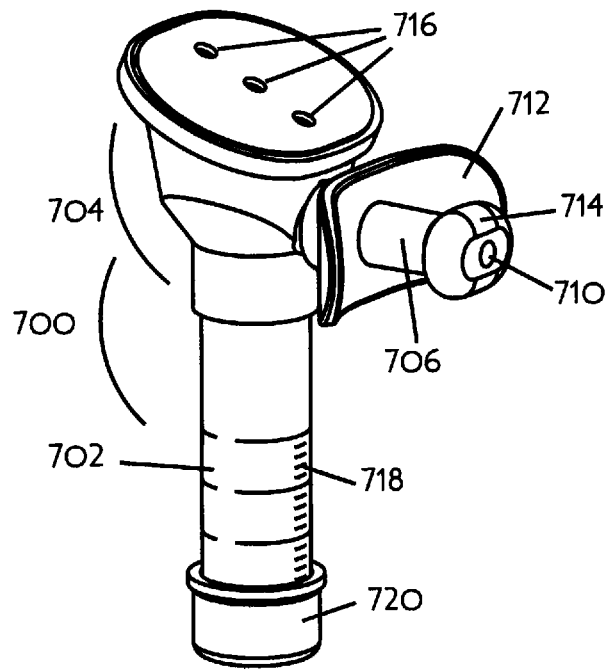
FIG. 7 is a perspective view showing an alternate embodiment of the present invention.

FIG. 7 shows an alternative embodiment of the present invention. Saliva collection device 700 includes a header assembly 704 and a collection vessel 702, which in this case need not be removably attached to header assembly 704. Mouthpiece 706 is attached to header assembly 704. Mouthpiece 706 includes saliva inlet 710, a mouthguard 712, and an enlargement 714, all of which function similarly to the embodiment shown in FIG. 1. Likewise, the embodiment of FIG. 7 may include a valve (not shown) as disclosed in the embodiment of FIG. 1, as well as gradations 718. Header assembly 704 has vent holes 716 and a venting membrane (not shown), also analogous to similar features in the embodiment of FIG. 1.

Figure 7A:
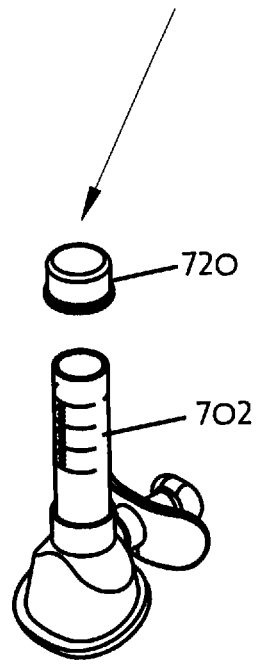
FIG. 7A is a perspective view showing additional functional details of the embodiment shown in FIG. 7.
Figure 7B:
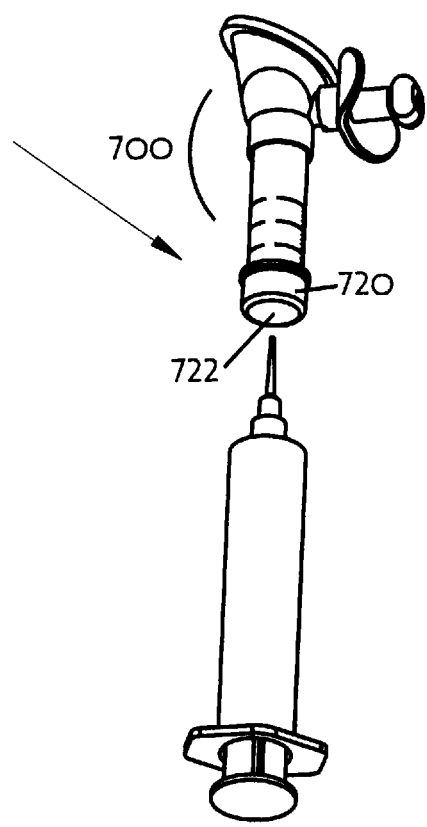
FIG. 7B is a perspective view of an example use of the embodiment shown in FIG. 7.

The embodiment of FIG. 7 includes seal cap 720, which allows access to the collected saliva in collection vessel 702. So, for example, seal cap 720 can be removed as shown in FIG. 7A after a successful saliva donation. Saliva can then be poured or pipetted out, for example. Alternatives to removable seal cap 720 to allow access to the collected saliva exist, and include a puncturable septum similar to a medicament vial with a rubber closure; a commonly available needle less connector, as is now typically used in intravenous infusion systems; a Luer taper fitting, onto which a removable plug is fitted; a frangible tip that can be snapped off to provide access; and a peelable or puncturable, sealed-foil covering. One such example, shown in FIG. 7B, is a puncture port accessible with syringe and needle or a pipette. In this case, seal cap 720 includes an access port 722. Regardless, the purpose of seal cap 720 is to provide access to collection vessel 702 through access port 722 for removing saliva.

Figure 8:
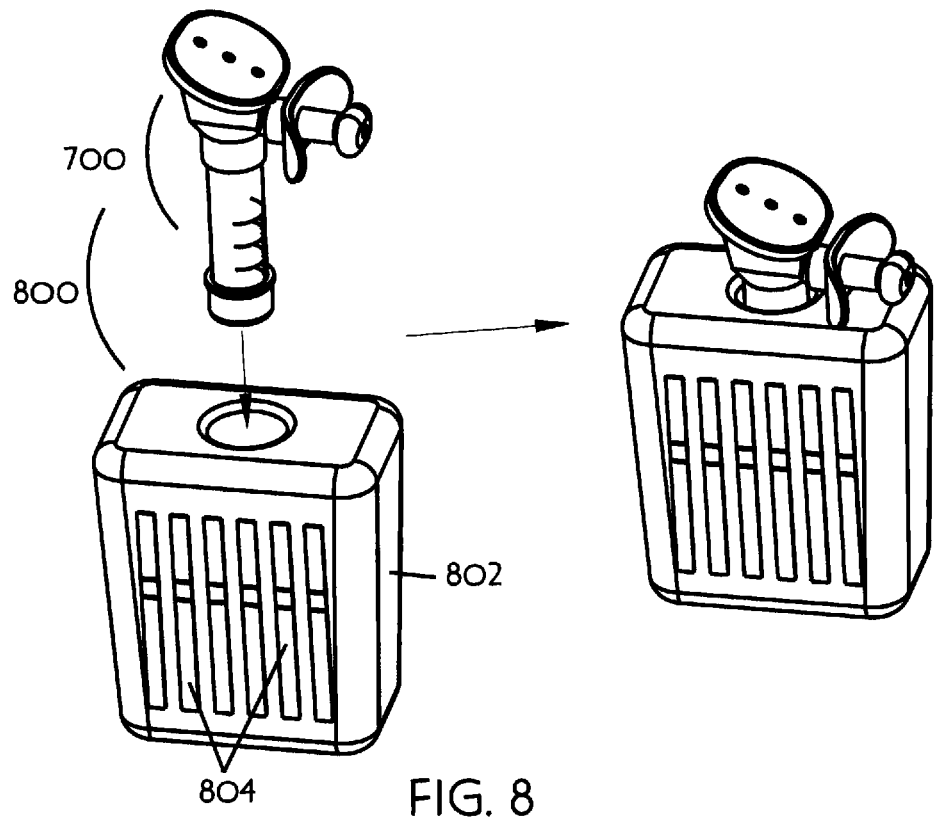
FIG. 8 is a multiple perspective view of an alternate example system using the present invention.

The embodiment shown in FIG. 7 can be used, for example as a component of an instant-read test for drugs of abuse. One such instant read system is shown in FIG. 8. Instant read system 800 includes a housing 802, which includes a plurality of lateral flow immunoassay test strips 804 internal to test housing 802, and visible to an observer. Saliva collection device 700, with features as previously described according to FIG. 7 includes an access port 722 (see FIG. 7B). Access port 722 can be, for example, a needleless connector, puncturable septum, or pierceable foil. A saliva collection device 700 that has been adequately filled with saliva is inserted into housing 802, which causes a fluid connection allowing test strips 804 to be exposed to saliva. Test methodology and reading of results is performed in accordance with normal practice for lateral flow immunoassay strip use.

Figure 9:
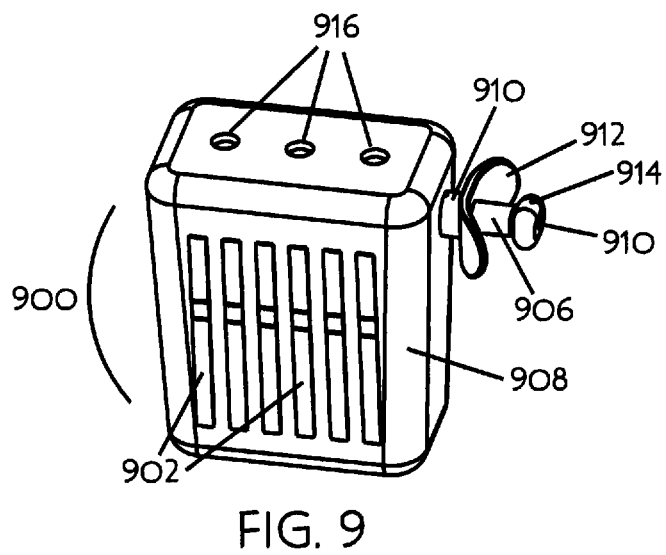
FIG. 9 is a perspective view of an alternate example system using the present invention.

Another alternative embodiment of a system for instant-read drugs of abuse testing that employs the present invention is shown in FIG. 9 as instant read system 900. In this embodiment, a housing 908 includes a plurality of lateral flow immunoassay test strips 902 internal to test housing 908, and visible to an observer. Integrally attached to housing 908 is a mouthpiece 906, which includes a saliva inlet 910. It can also include a mouthguard 912 and enlargement 914, which are analogous to structures previously described. Housing 908 includes vent holes 916, which vent expectorated air as in previously described embodiments. Also, as previously described, instant read system 900 includes an internal collection vessel (not shown), and may include a valve between the saliva inlet 910 and the collection vessel. As before, collected saliva is allowed to communicate with the test strips 902, and the test methodology and reading of results is performed in accordance with normal practice for lateral flow immunoassay strip use.

The above disclosure is related to the detailed technical contents and inventive futures thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered by the spirit and technical theory of the subject invention.

The invention claimed is:

1. A device for collecting oral fluid comprising: an upper header assembly and a collection vessel removably attachable to the upper header assembly, the collection vessel defining a vertical axis extending through the upper header assembly when attached to the upper header assembly, the upper header assembly comprising:
  a header housing defining a header chamber therein, the housing comprising an upwardly oriented vent face portion having at least one vent opening with a hydrophobic filter adjacent thereto;
  the header housing including a converging portion defining a converging portion of the header chamber, the converging portion of the header housing extending to a lower receptacle portion defining a header chamber lower outlet where the collection vessel attaches, the header housing having a side inlet connecting to a mouthpiece extending laterally from the header housing, the upwardly oriented vent face portion positioned above the side inlet, the mouthpiece shaped to be received by a mouth and having a saliva inlet connecting to the header chamber by way of a passageway, the header housing having an upright wall opposite the side inlet;
  the collection vessel removably engaged with the lower receptacle portion whereby saliva received in the header chamber can flow by gravity into the collection vessel and the filter is positioned above the side inlet.

2. The device of claim 1 wherein the upwardly oriented vent face portion is generally planar and defines an upper chamber wall traversed by the hydrophobic filter.

3. The device of claim 1 wherein the filter comprises polytetrafluoroethylene.

4. The device of claim 1 wherein the mouthpiece includes a shaft extending from the housing and a mouth guard extending from the shaft, the saliva passageway extending through the shaft.

5. The device of claim 1 further comprising a valve positioned in the device along the saliva passageway and captured by the mouthpiece.

6. The device of claim 5 wherein the valve is a one way valve to allow saliva to pass into the header chamber from the saliva inlet but not from the header chamber to the inlet.

7. The device of claim 1 further comprising an access means for the collection vessel, the access means comprising one of the set of: a removable plug, a Luer connector and Luer plug, a needle-free access port, a pierceable area, a peelable strip, a frangible tab, and a separable portion of the collection vessel.

8. The device of claim 1 wherein the vessel is a configured as a transparent vial and has gradations thereon and threadingly attaches to the lower receptacle portion.

9. A device for collecting oral fluid comprising:
  an upper header assembly and a collection vessel removably attached to the upper header assembly, the upper header assembly comprising:
    a header housing defining a header chamber therein, the housing comprising an upwardly oriented vent face portion having at least one vent opening with a hydrophobic filter adjacent thereto; a converging portion extending from the vent face, the converging portion defining a converging portion of the chamber, the converging portion extending to a lower receptacle portion defining a header chamber lower outlet, a mouthpiece extending from the header housing, the mouthpiece shaped to be received by a mouth and having a saliva inlet connecting to the header chamber by way of a passageway;
    the collection vessel removably engaged with the lower receptacle portion whereby saliva in the header chamber can flow by gravity into the collection vessel;
    wherein the device has a vertical axis and the area of the hydrophobic filter is greater than the area of a cross-section of the header portion chamber taken at a plane perpendicular to the axis of the device.

10. A device for collecting oral fluid comprising:
  an upper header assembly and a collection vessel removably attached to the upper header assembly, the upper header assembly comprising:
    a header housing defining a header chamber therein, the housing comprising an upwardly oriented vent face portion having at least one vent opening with a hydrophobic filter adjacent thereto; a converging portion extending from the vent face, the converging portion defining a converging portion of the chamber, the converging portion extending to a lower receptacle portion defining a header chamber lower outlet, a mouthpiece extending from the header housing, the mouthpiece shaped to be received by a mouth and having a saliva inlet connecting to the header chamber by way of a passageway;
    the collection vessel removably engaged with the lower receptacle portion whereby saliva in the header chamber can flow by gravity into the collection vessel;
    wherein the device has a vertical axis and the vent face and the hydrophobic filter are arranged at an oblique angle from horizontal.

11. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, wherein the valve is a one way valve to allow saliva to pass into the header chamber from the saliva inlet but not from the header chamber to the inlet and the valve is captured by the mouthpiece at the header inlet.

12. The device of claim 11 wherein the valve is a duckbill valve.

13. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, wherein the housing comprises an upwardly oriented vent face portion and the vent is positioned thereat, the vent face portion being generally planar and part of an upper chamber wall traversed by a hydrophobic filter.

14. A device for collecting oral fluid comprising:
an upper header assembly and a collection vessel removably attached to the upper header assembly, the upper header assembly comprising:
a header housing defining a header chamber therein, the housing having at least one vent opening extending from the header chamber to exterior the device, the header housing comprising a lower receptacle portion defining a header chamber lower outlet, a mouthpiece extending from the header housing, the mouthpiece shaped to be received by a mouth and having a saliva inlet connecting to the header chamber by way of a saliva passageway; a valve positioned in the device at the saliva passageway;
the collection vessel removably engaged with the lower receptacle portion;
wherein the device has a vertical axis and a hydrophobic filter configured as a layer at the vent, the area of the hydrophobic filter is greater than an area of a cross-section of the header portion chamber taken at a plane perpendicular to the axis of the device.

15. The device of claim 14 wherein the filter comprises polytetrafluoroethylene.

16. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, wherein the vent has a hydrophobic filter adjacent thereto and the hydrophobic filter has an dimensional area exposed to the interior of the header chamber and the vessel has a horizontal cross sectional area and the area exposed to the interior of the header chamber is at least twice the horizontal cross sectional area of the vessel.

17. The device of claim 16 wherein the hydrophobic filter has an area exposed to the interior of the header chamber and the header chamber has a maximum horizontal cross sectional area and the area exposed to the interior of the header chamber is equal to or greater that the maximum horizontal cross sectional area of the header chamber.

18. The device of claim 16 wherein the hydrophobic filter has an area exposed to the interior of the header chamber and the header chamber has a maximum horizontal cross sectional area and the area exposed to the interior of the header chamber is at least half of the horizontal cross sectional area of the vessel.

19. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, wherein the mouthpiece includes a shaft extending from the housing and a mouth guard extending from the shaft, the saliva passageway extending through the shaft.

20. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, the device further comprising an access means for the collection vessel, the access means comprising one of the set of: a removable plug, a Luer connector and Luer plug, a needle-free access port, a pierceable area, a peelable strip, a frangible tab, and a separable portion of the collection vessel.

21. The device of claim 20 wherein the mouthpiece includes a mouthguard, said mouthguard providing a stop at a proper insertion depth in the mouth.

22. The device of claim 20 wherein said access means further comprises a tamper-evident means.

23. A device for collecting oral fluid comprising: an upper header assembly and a collection vessel removably attached to the upper header assembly, the collection vessel having a vertical axis, the upper header assembly comprising: a header housing defining a header chamber therein, the housing having at least one vent opening extending from the header chamber to exterior the device, the header housing comprising a lower receptacle portion defining a header chamber lower outlet for connection to the collection vessel, the header housing having a side inlet with a mouthpiece extending horizontally therefrom, the mouthpiece shaped to be received by a mouth and having a saliva inlet connecting to the header chamber by way of a saliva passageway, the saliva passageway extending straight and horizontally from the saliva inlet into the header chamber; a check valve positioned in the device at the saliva passageway; the collection vessel removably engaged with the lower receptacle portion, the device further comprising at least one of the following:

preservatives, anti-foaming agents, and chemical test reagents.

\* \* \* \* \*